United States Patent [19]

Perricone

[11] Patent Number: 5,376,361

[45] Date of Patent: Dec. 27, 1994

[54] METHOD AND COMPOSITIONS FOR TOPICAL APPLICATION TO THE SKIN FOR PREVENTION AND/OR TREATMENT OF RADIATION-INDUCED SKIN DAMAGE

[76] Inventor: Nicholas V. Perricone, 27 Coginchaug Ct., Guilford, Conn. 06437

[21] Appl. No.: 3,603

[22] Filed: Jan. 13, 1993

[51] Int. Cl.⁵ .................. A61K 7/42; A61K 7/44; A61K 31/34
[52] U.S. Cl. .................. 424/59; 424/60; 514/474
[58] Field of Search .................. 424/59, 60; 514/474

[56] References Cited

U.S. PATENT DOCUMENTS

| | | | |
|---|---|---|---|
| 4,695,452 | 9/1987 | Gannis et al. | 514/474 |
| 4,938,969 | 7/1990 | Schinitsky et al. | 514/474 |
| 4,975,272 | 12/1990 | Voyt | 514/886 |
| 4,983,382 | 1/1991 | Wilmott et al. | 424/62 |

FOREIGN PATENT DOCUMENTS

| | | | |
|---|---|---|---|
| 291960 | 11/1988 | European Pat. Off. | A61K 7/00 |
| 337464 | 10/1989 | European Pat. Off. | A61K 7/00 |
| 2000507 | 7/1970 | Germany | A61K 7/00 |
| 52-61239 | 5/1977 | Japan | A61K 7/32 |
| 1152613 | 7/1986 | Japan | 424/63 |
| ZA75/6475 | 5/1976 | South Africa | A61K 7/00 |

OTHER PUBLICATIONS

Encyclopedia of Chem. Technology, 3rd ed. vol. 20, pp. 762–763, 1982.
Grant & Hackh's Chemical Dictionary, 5th ed., pp. 529–530, 1987.

Primary Examiner—Dale R. Ore
Attorney, Agent, or Firm—St. Onge Steward Johnston & Reens

[57] ABSTRACT

A method for the prevention and/or treatment of radiation-induced skin damage, particularly ultraviolet-induced skin burn (e.g., sunburn), in which a tocotrienol, a derivative thereof or a vitamin E preparation enriched with tocotrienol or a tocotrienol derivative, is topically applied to the exposed or affected skin areas. A fat-soluble fatty acid ester of ascorbic acid such as palmityl ascorbate is preferably applied with the tocotrienol in association with a dermatologically acceptable carrier. Tocotrienol augments the efficacy of sunscreens containing compounds that reduce penetration of or absorb ultraviolet radiation.

20 Claims, No Drawings

METHOD AND COMPOSITIONS FOR TOPICAL APPLICATION TO THE SKIN FOR PREVENTION AND/OR TREATMENT OF RADIATION-INDUCED SKIN DAMAGE

DESCRIPTION

1. Technical Field

The present invention relates to the topical application to the skin of active agents, and/or preparations containing them, for the prevention and/or treatment of radiation damage to the skin, and particularly for the treatment of skin to protect it from deleterious effects caused by excessive exposure to ultraviolet radiation, as in the case of sunburn.

2. Background Art

Ultraviolet-induced burning of the skin is most commonly seen in persons who have been excessively exposed to natural sunlight (i.e., sunburn), but also can be seen in persons who have been excessively exposed to ultraviolet radiation from non-sunlight (artificial) sources, as may occur in tanning booths or incident to application of ultraviolet radiation as part of a therapeutic treatment. Cutaneous burn and other forms of skin damage also can arise from excessive or prolonged exposure to other forms of radiation outside the ultraviolet spectrum.

The clinical manifestations of ultraviolet-induced burn seen in acute reactions is attributed to ultraviolet radiation in the range of 290-320 nanometers, generally designated ultraviolet B (UVB) radiation, although prolonged exposure to longer wavelength ultraviolet A light (~320-400 nanometers) can produce mild burn and marked hyperpigmentation.

The sunburn reaction is a complex inflammatory process causing dyskeratotic cells, spongiosis, vacuolation of kertinocytes and edema from capillary leakage, 12 to 24 hours after exposure to light. In addition to redness and pain, blisters may evolve. Chronic effects of UV light include degenerative changes of the skin which can lead to premalignant and malignant growths of the skin and degeneration of the dermal collagen.

The detrimental effects of sunburn have been postulated to be related to a transfer of energy from ultraviolet radiation to the skin, resulting in generation of excited oxygen species, such as singlet oxygen, the superoxide anion, and hydroxyl radicals that can damage lipid-rich membranes with the subsequent activation of the chemical mediators of inflammation. It is well known that ultraviolet B radiation releases arachidonic acid, which is quickly oxidized to a variety of biologically active metabolites, such as prostaglandins PGD2, PGE2, PGEF2. When arachadonic acid is oxidized via the cyclo-oxygenase pathway, prostaglandins create marked erythema. Arachadonic acid oxidized via the 5-lipo-oxygenase pathway produces leukotrienes, which also can cause erythema and edema. The free radicals created by ultraviolet radiation can also damage the DNA of the cells, resulting in permanent injury, premature aging, and carcinogenesis.

The clinical symptoms of ultraviolet burn are on a spectrum from mild increased sensitivity of the skin to severe pain. It should also be noted that damage to skin can be caused by other forms of radiation, that is, ionizing radiation as well as longer wave length radiation such as infrared, which can result in erythema and pigmentation as well as premature aging and malignancy. These other forms of radiation create damage by the same mechanism, i.e., generation of free radicals with subsequent damage to the cell membrane and DNA.

Suggestions for dealing with sunburn and other forms of ultraviolet radiation burn have predominantly been aimed at prevention through use of topical compositions containing agents for absorbing radiation, e.g., as exemplified by commercial sunscreen products. More recently, attention has been directed to agents which address the underlying processes involved in radiation-induced skin damage, such as the earlier-noted free radical generation processes. In this regard, investigations have been made with respect to the antioxidants vitamin E and vitamin C to quench free radicals on the surface of the skin and to protect lipid membranes intracellularly (Wilson, R., *Drug and Cosmetic Industry*, 32-34, 38, and 68, August 1992).

Vitamin E is a fat-soluble vitamin necessary in the diet of many species for normal reproduction, normal development of muscles, normal resistance of erythrocytes to hemolysis, and various other biochemical functions. The most widely accepted function of vitamin E is an an antioxidant, protecting polyunsaturated fatty acids in membranes and other cellular structures from attack by free radicals. Vitamin E occurs in cereals (especially wheat germ and corn), sunflower seed, rapeseed, soybean oil, alfalfa, lettuce, egg yolk, and beef liver, and consists primarily of three molecular species of tocol derivatives, the alpha-, beta- and gamma-tocopherols, of which alpha-tocopherol is most important because it has the widest distribution and greatest biological activity.

Other tocopherols have been found in nature, including gamma-, eta-, zeta$_2$, zeta$_1$- and epsilon-tocopherol. The last two species, which occur in cereal grains, have unsaturated hydrocarbon tails and have been recently called tocotrienols (denoted alpha- and beta-tocotrienol, respectively) because each has three double bonds in the side chain, and this nomenclature distinguishes them from tocopherols bearing saturated tails. Gamma-tocopherol is claimed to be the most potent antioxidant of any tocopherol species (*The Merck Index*, 11th ed., 1989, entries 9417 to 9423 and 9931), but activity appears to be dependent on the system used for measurement. Thus, in the in vitro systems of Burton, G. W., et al., *J. Am. Chem. Soc.* 107:7073-7065 (1985), for example, alpha-tocopherol was the most powerful antioxidant.

The antioxidant function of vitamin E per se is localized in the chromanol nucleus, where the phenolic hydroxy group donates a hydrogen atom to quench lipid radicals ibid., and Serbinova, E., et al., *Free Radical Biology & Med.*, 10:263-275 (1991)). The antioxidant potency of vitamin E is determined by the efficiency of the tocopherol in scavenging radicals and by the reactivity of the chromanoxyl radical formed in further propagation of lipid peroxidation or in the regeneration of the tocopherol due to interaction of the chromanoxyl radical with reductants; the latter does not propagate lipid peroxidation.

In homogenous solutions, the rate constants of the reaction between the chromanol nucleus and radicals do not depend upon the length or unsaturation of the tocopherol hydrocarbon tails, but mainly depend on the number of methyl groups in the benzene ring of the chromanol nucleus (Burton, G. W., et al., cited above). Similarly, the reactivity of the chromanoxyl radical is mainly determined by hindering effects of the methyl groups.

The situation is more complex in heterogenous membrane systems, however, where vitamin E appears to owe its antioxidant potency not solely to the chemistry of the tocopherol molecule but also to its mobility and accessibility within the membrane (Serbinova, cited above). In some systems, tocotrienols appear to have higher antioxidant activity (ibid.). However, in others, direct comparisons of antioxidant efficiency of tocopherols having saturated tails with tocotrienols did not demonstrate decisive differences in the activities of these two forms of vitamin E (ibid. and Nakano, M., et al., *Biochim. Biophys. Acta* 619:274–286 (1980)).

DISCLOSURE OF THE INVENTION

The primary object of this invention is to provide methods and compositions for prevention and/or treatment of radiation skin burn, particularly ultraviolet skin burn, and most particularly sunburn.

It is a more particular object of the invention to provide a preventive regimen and/or therapy based upon topical application to exposed or affected skin areas of an active agent or precursor thereof, preferably in association with a dermatologically acceptable carrier or vehicle such as a sunscreen.

These and other objects are accomplished by the present invention, which provides a method and composition for the prevention and/or treatment of radiation-induced skin damage, which comprises topical application to the exposed or affected skin sites of an effective amount of one or more tocotrienols or derivatives thereof or vitamin E compositions enriched with tocotrienols or tocotrienol derivatives. Reductants such as alpha-hydroxy acids, ascorbic acid and the like, particularly fat-soluble fatty acid esters of ascorbic acid, can, optionally, be utilized along with the tocotrienol as a means for yet further enhancing the efficacy of the therapeutic or prophylactic treatment.

In the preferred practice of the invention, the tocotrienol (or derivative) or tocotrienol-enriched vitamin E is applied in admixture with a dermatologically acceptable carrier or vehicle (e.g., as a lotion, cream, ointment, soap, or the like) so as to facilitate topical application and, in some cases, provide additional therapeutic effects as might be brought about, e.g., by moisturizing of the affected skin areas. As noted, reductants, particularly ascorbyl fatty acid esters, e.g., ascorbyl palmitate, can be advantageously included in the compositions. In some embodiments, the dermatologically acceptable carrier is a sunscreen composition.

The amount of tocotrienol or derivative thereof (hereinafter referred to collectively as tocotrienol for ease of reference) necessary to bring about enhanced prevention and/or therapeutic treatment of radiation-induced skin damage is not fixed per se, and necessarily is dependent upon the identity and form of tocotrienol employed, the concentration of tocotrienol when employed as a tocotrienol-enriched vitamin E preparation and/or with a carrier, the amount and type of any additional reductant such as ascorbyl fatty acid ester, when employed with the tocotrienol, the user's skin type, and, where present, the severity and extent of the patient's pathological skin condition. Generally, the tocotrienol or composition containing it is topically applied in effective amounts to skin areas which have been damaged or aged, or which are susceptible to damage, by reason of radiation, especially ultraviolet radiation.

BEST MODES FOR CARRYING OUT THE INVENTION

This invention is based upon the surprising finding that tocotrienols or tocotrienol-enriched vitamin E compositions, especially tocotrienols or tocotrienol-enriched vitamin E in combination with a reductant, such as ascorbyl fatty acid ester, augment the efficacy of sunscreens, including sunscreens that contain ordinary vitamin E.

As used herein, the term "tocopherol" encompasses vitamin E derivatives bearing saturated hydrocarbon tails having the following general formula:

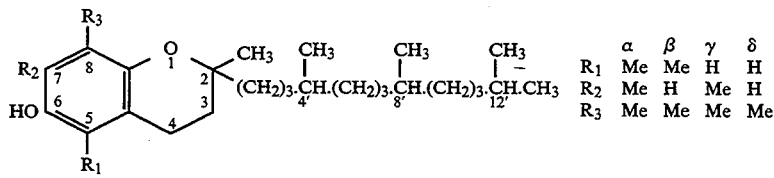

and includes both natural alpha-, beta-, gamma-, and delta-tocopherol as well as synthetic derivatives and mixtures thereof. The term "tocotrienol" encompasses their counter-parts bearing unsaturated tails, including, but not limited to, four tocotrienols occurring in sunflower seeds and vegetable oils and in African violets, which have three double bonds in the side chain at the 3', 7' and 11' positions in the formula set out above, denoted alpha-, beta-, gamma- and delta-tocotrienol, their synthetic counterparts, and mixtures thereof. The double bonds may be cis or trans or mixtures thereof.

Tocotrienol or tocotrienol derivatives or mixtures thereof are employed in this invention either in the substantial absence of tocopherols wherein the compositions contain essentially no tocopherol or in tocotrienol-enriched vitamin E preparations. By "tocotrienol-enriched vitamin E preparations" is meant vitamin E preparations containing a greater concentration of tocotrienol than that found in preparations isolated from natural sources. These tocotrienol-enriched vitamin E preparations can, for example, be naturally-occurring vitamin E preparations to which tocotrienol has been added or naturally occurring vitamin E preparations from which a portion of tocopherol has been removed.

Preferred vitamin E preparations are isolated from natural sources, but synthetic preparations may also be employed as well as mixtures of natural and synthetic vitamin E. Tocotrienol-enriched vitamin E preparations may be obtained by fractionating vitamin E preparations to remove a portion of tocopherols and recover a preparation more highly concentrated in tocotrienol. Preferred tocotrienols are natural products isolated, for example, from wheat germ oil, bran, or palm oil using high performance liquid chromatography. D-alpha-tocotrienol is especially preferred in one embodiment.

As with other vitamin E preparations, tocotrienol or tocotrienol-enriched preparations include those containing tocotrienol and, in some cases, tocopherol derivatives. These typically include derivatives related to the phenolic hydroxyl functionality, i.e., wherein it is reacted with an acid to form an ester such as an acetate. However, the derivatives may also include those involving other reactive groups known to those skilled in the art. Where tocotrienol derivatives are employed, they must be functionally equivalent to tocotrienol. Preferred derivatives contain both the chromanol nucleus and three double bonds in the hydrocarbon tail.

Vitamin E derivatives generally vary in consistency from viscous oils to oily liquids. Therefore, tocotrienols or tocotrienol-enriched vitamin E preparations can be applied neat to skin areas subject to damage or damaged by radiation. However, only effective amounts of tocotrienols are needed to prevent or treat radiation-induced skin damage, so generally topical application to exposed or affected skin sites is accomplished in association with a carrier, and particularly one in which the active ingredient is soluble per se or is effectively solubilized (e.g., as an emulsion or microemulsion). It is necessary that the carrier be inert in the sense of not bringing about a deactivation of the tocotrienol or derivative, and in the sense of not bringing about any adverse effect on the skin areas to which it is applied.

Suitable carriers include water, alcohols, oils and the like, chosen for their ability to dissolve or disperse the active ingredient at concentrations of active ingredient most suitable for use in the preventive or therapeutic treatment. Generally, even low concentrations of active ingredient in a carrier will be suitable, requiring only that more frequent topical application be resorted to. As a practical matter, however, to avoid the need for repeated application, it is desirable that the topically applied composition (i.e., tocotrienol or derivative or tocotrienol-enriched vitamin E preparation plus carrier) be formulated to contain at least about 0.5% by weight, and in some embodiments at least about 3% by weight, and in other embodiments at least about 3 to 10% by weight, of the active ingredient, and accordingly, carriers will be chosen which can solubilize or disperse the active ingredient at such concentrations.

While the carrier for the tocotrienol or derivative or tocotrienol-enriched vitamin E preparation can consist of a relatively simple solvent or dispersant such as water or oils, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many such compositions are known in the art, and can take the form of lotions, creams, gels or even solid compositions (e.g., stick-form preparations). Typical compositions include lotions containing water and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as dermatologically acceptable carriers.

Many preferred embodiments of this invention contain a reductant in addition to tocotrienol. Some embodiments, for example, employ alpha-hydroxy acids such as glycolic acid, hydroxymethylglycolic acid, lactic acid, glucuronic acid, galacturonic acid, gluconic acid, glucoheptonic acid, alpha-hydroxybutyric acid, alpha-hydroxyisobutyric acid, alpha-hydroxyvaleric acid, alpha-hydroxyisovaleric acid, alpha-hydroxycaproic acid, alpha-isocaproic acid, tartronic acid, tartaric acid, malic acid, hydroxyglutaric acid, hydroxyadipic acid, hydroxypimelic acid, muric acid, citric acid, isocitric acid, saccharic acid, dihydroxymaleic acid, dihydroxytartaric acid, and dihydroxyfumaric acid or derivatives of hydroxy acids such as pyruvic acid, methyl pyrivate, ethyl pyruvate, isopropyl pyruvate, benzoylformic acid, methyl benzoylformate, and ethyl benzoylformate.

Other embodiments employ ascorbic acid as a reductant, most preferably fat-soluble fatty acid esters of ascorbic acid (vitamin C) in addition to tocotrienol. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate.

The combination of tocotrienol or tocotrienol-enriched vitamin E preparations and a fat-soluble vitamin C fatty acid ester in a dermatologically acceptable carrier is especially advantageous in sunscreen compositions, because tocotrienol augments the efficacy of sunscreens. By "sun-screen" is meant any topical preparation containing a substance that absorbs or reduces penetration of ultraviolet radiation partially, such as, for example compositions containing para-aminobenzoic acid and/or its esters, cinnamates, benzophenone, anthranilate, and the like, or totally, such as, for example, compositions containing titanium dioxide, zinc oxide, iron oxide, and the like. Preferred sunscreens formulated with tocotrienol according to this invention have a sun protective factor (SPF) of at least 3, most preferably from at least about 6 to about 23.

The effectiveness of tocotrienols and tocotrienol derivatives, especially when employed in combination with a reductant such as ascorbyl fatty acid esters, can be postulated as resulting from the antioxidant properties of tocotrienol per se, which properties are unexpectedly retained and provided to a high degree when used in concert with ascorbyl fatty acid esters when these are delivered in combination to the skin in an extremely effective manner in an oil phase. The mechanism of the effect is not well understood, but may be related to the anti-oxidant properties of the active compounds and/or their interference with chemical reactions.

In terms of a possible explanation for the effectiveness of tocotrienol in the prevention or treatment of radiation damage to the skin, it is noted that tocotrienol, as an antioxidant, can scavenge free radicals such as the oxygen radicals created by exposure of cells to radiation, as well as the generation of free radicals produced by normal metabolism extracellularly and intracellularly. Ascorbic acid is a powerful reducing agent that can prevent oxidative damage and regenerate chromanoxyl radicals formed as vitamin E derivatives scavenge radicals, reforming vitamin E that can scavenge more radicals. Preferred embodiments of this invention harness this synergestic effect.

In addition, ascorbic acid can increase cyclo-oxygenase activity in human cells. Cyclo-oxygenase is a key enzyme in the oxidation of arachadonic acid, which leads the formation of prostaglandins which in turn mediate inflammation.

The method of the present invention is particularly useful for the prevention of skin damage which may result from exposure to ultraviolet radiation, but, based upon the likely mechanism of action, also is useful in general for treatment of any radiation-induced skin damage, particularly that associated with free radical related damage. As such, the topical application of tocotrienol according to the invention can also be effective for chronic administration to prevent the free radical damage seen in the natural aging process of the skin and the free radical damage caused by chronic exposure to sunlight. Tocotrienol or tocotrienol and ascorbyl fatty acid esters can thus be added to dermatological creams and emollients as well as to commercial sunscreens to enhance their anti-aging and anti-cancer activity. It can also be applied as a treatment after burn.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims.

We claim:

1. A method for preventing radiation-induced skin damage, said method comprising topically applying to skin areas subject to such damage an effective amount of an active ingredient selected from the group consisting of tocotrienols and vitamin E preparations enriched with tocotrienols.

2. A method according to claim 1 wherein the active ingredient is a tocotrienol selected from the group consisting of alpha-tocotrienol, beta-tocotrienol, gamma-tocotrienol, and delta-tocotrienol.

3. A method according to claim 1 wherein said effective amount is applied as a composition further comprising a reductant.

4. A method according to claim 3 wherein said reductant is a fat-soluble fatty acid ester of ascorbic acid.

5. A method according to claim 4 wherein said fat-soluble fatty acid ester of ascorbic acid is selected from the group consisting of ascorbyl palmitate, ascorbyl laurate, ascorbyl myristate, ascorbyl stearate, and mixtures thereof.

6. A method according to claim 5 wherein said fat-soluble fatty acid ester of ascorbic acid is ascorbyl palmitate.

7. A method according to claim 1 wherein said active compound is applied in the form of a sunscreen composition further comprising a dermatologically acceptable carrier.

8. A method according to claim 7 wherein the sunscreen composition contains a compound that reduces penetration of or absorbs ultraviolet radiation.

9. A method according to claim 8 wherein the compound that reduces penetration of or absorbs ultraviolet radiation is selected from the group consisting of para-aminobenzoic acid, para-aminobenzoic acid esters, cinnamates, benzophenone, anthranilate, titanium dioxide, zinc oxide, iron oxide, and mixtures thereof.

10. A method according to claim 7 wherein the combination of the compound and the carrier is in a form selected from the group consisting of solutions, dispersions, creams, lotions, gels and solid sticks.

11. A method according to claim 7 wherein the combination comprises about 0.5% to about 5% by weight tocotrienol.

12. A method for the treatment of radiation-induced skin damage, said treatment comprising topically applying to the affected skin areas an effective amount of a composition comprised of a dermatologically acceptable carrier and a tocotrienol composition selected from the group consisting of
 tocotrienols,
 and a vitamin E preparation enriched with tocotrienols.

13. A method according to claim 12 wherein the composition further comprises a fat-soluble fatty acid ester of ascorbic acid selected from the group consisting of ascorbyl palmitate, ascorbyl laurate, ascorbyl myristate, ascorbyl stearate, and mixtures thereof.

14. A method according to claim 12 wherein the tocotrienol is selected from the group consisting of alpha-tocotrienol, beta-tocotrienol, gamma-tocotrienol, and delta-tocotrienol.

15. A method according to claim 14 wherein the tocotrienol is alpha-tocotrienol.

16. In a sunscreen composition comprising a compound that reduces penetration of or absorbs ultraviolet radiation and a dermatologically acceptable carrier, an improvement wherein, to augment the efficacy of the sunscreen, said composition further comprises a tocotrienol composition selected from the group consisting of tocotrienols and vitamin E preparations enriched with tocotrienols.

17. An improvement according to claim 16 wherein said tocotrienol is selected from the group consisting of alpha-tocotrienol, beta-tocotrienol, gamma-tocotrienol, and delta-tocotrienol.

18. An improvement according to claim 16 wherein the compound that reduces penetration of or absorbs ultraviolet radiation is selected from .the group consisting of para-aminobenzoic acid, para-aminobenzoic acid esters, cinnamates, benzophenone, anthranilate, titanium dioxide, zinc oxide, iron oxide, and mixtures thereof.

19. An improvement according to claim 16 wherein the composition further comprises a fat-soluble fatty acid ester of ascorbic acid selected from the group consisting of ascorbyl palmitate, ascorbyl laurate, ascorbyl myristate, ascorbyl stearate, and mixtures thereof.

20. An improvement according to claim 19 wherein said tocotrienol is D-alpha-tocotrienol.

* * * * *